United States Patent
Schanze

(10) Patent No.: US 10,765,885 B2
(45) Date of Patent: Sep. 8, 2020

(54) PHOTOTHERAPY MASK WITH QUANTUM DOT PHOSPHORS

(71) Applicant: Nanoco Technologies Ltd., Manchester (GB)

(72) Inventor: Torsten Schanze, Manchester (GB)

(73) Assignee: Nanoco Technologies Ltd., Manchester (GB)

( * ) Notice: Subject to any disclaimer, the term of this patent is extended or adjusted under 35 U.S.C. 154(b) by 146 days.

(21) Appl. No.: 15/441,460

(22) Filed: Feb. 24, 2017

(65) Prior Publication Data
US 2017/0246474 A1    Aug. 31, 2017

Related U.S. Application Data

(60) Provisional application No. 62/300,484, filed on Feb. 26, 2016.

(51) Int. Cl.
*A61N 5/06*    (2006.01)

(52) U.S. Cl.
CPC .... *A61N 5/0616* (2013.01); *A61N 2005/0647* (2013.01); *A61N 2005/0652* (2013.01); *A61N 2005/0659* (2013.01); *A61N 2005/0661* (2013.01); *A61N 2005/0662* (2013.01); *A61N 2005/0663* (2013.01)

(58) Field of Classification Search
CPC ...................... A61N 2005/0647; A61N 5/0616
USPC .......................................................... 607/91
See application file for complete search history.

(56) References Cited

U.S. PATENT DOCUMENTS

| | | | | |
|---|---|---|---|---|
| 2005/0070977 | A1* | 3/2005 | Molina | A61N 2/002 607/88 |
| 2005/0080465 | A1* | 4/2005 | Zelickson | A61N 5/0616 607/88 |
| 2007/0239232 | A1* | 10/2007 | Kurtz | G02B 6/001 607/87 |
| 2007/0276455 | A1* | 11/2007 | Fiset | A61C 19/066 607/91 |
| 2011/0040355 | A1* | 2/2011 | Francis | A61N 5/0616 607/88 |
| 2013/0304162 | A1* | 11/2013 | Veres | A61N 5/0613 607/88 |

(Continued)

FOREIGN PATENT DOCUMENTS

| | | | |
|---|---|---|---|
| WO | 2010078581 | A1 | 7/2010 |
| WO | 2012127389 | A1 | 9/2012 |

(Continued)

*Primary Examiner* — Gary Jackson
*Assistant Examiner* — Zahed Kabir
(74) *Attorney, Agent, or Firm* — Blank Rome, LLP

(57) ABSTRACT

A phototherapy device comprises a face mask having a rigid (or semi-rigid) shell contoured to the human face. A flexible array of LEDs is affixed to the inner surface of the mask. A flexible, quantum dot-containing film is situated over the flexible array of LEDs. The quantum dots in the QD-containing film are selected to photo-luminesce at one or more particular wavelengths in response to photoexcitation by the light emitted from the LEDs. The LEDs emit "primary light" and the quantum dots down-convert at least a portion of the primary light to "secondary light." The flexible, quantum dot-containing film may be interchangeable such that the wavelength(s) of the secondary light may be tailored to various phototherapy treatment regimes.

14 Claims, 2 Drawing Sheets

(56) References Cited

U.S. PATENT DOCUMENTS

| | | | |
|---|---|---|---|
| 2014/0005757 A1* | 1/2014 | English | A61N 5/06 607/91 |
| 2014/0277297 A1 | 9/2014 | Harris et al. | |
| 2015/0047765 A1* | 2/2015 | Vo | B32B 37/24 156/60 |
| 2015/0054945 A1* | 2/2015 | Bangera | A61B 10/02 348/135 |
| 2015/0067948 A1* | 3/2015 | Jackson | A41G 7/00 2/173 |
| 2015/0275078 A1 | 10/2015 | Vo et al. | |
| 2016/0000208 A1* | 1/2016 | Wong | A45D 44/002 132/320 |
| 2016/0158569 A1* | 6/2016 | Mofar | A61N 2/002 600/14 |
| 2017/0233644 A1 | 8/2017 | Amilcar et al. | |
| 2017/0246076 A1* | 8/2017 | Miller | A61H 23/02 |

FOREIGN PATENT DOCUMENTS

| | | | |
|---|---|---|---|
| WO | 2013105007 A1 | 7/2013 | |
| WO | 2014146029 A1 | 9/2014 | |

* cited by examiner

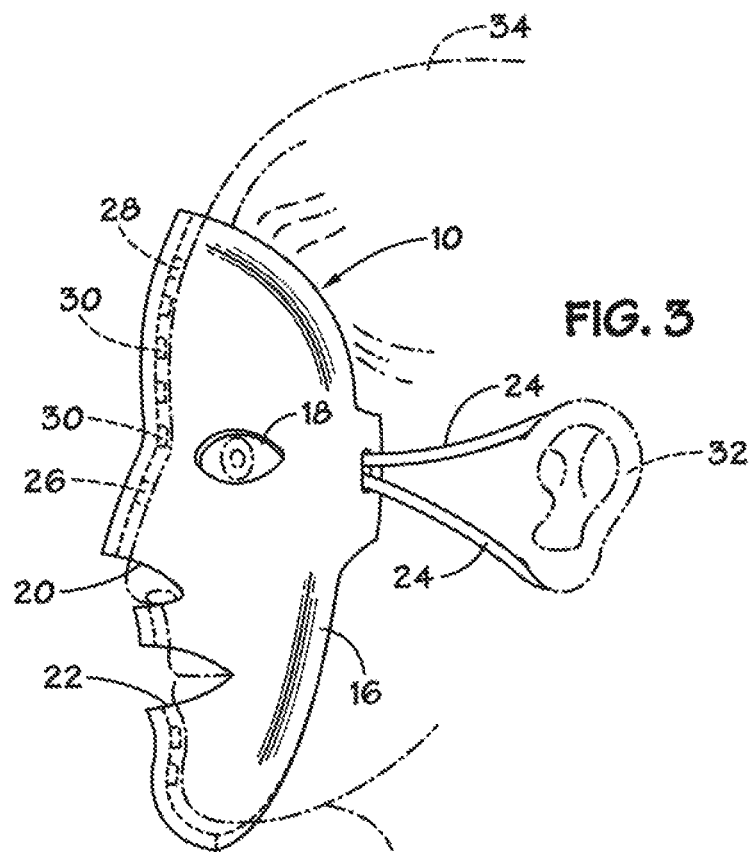
FIG. 3
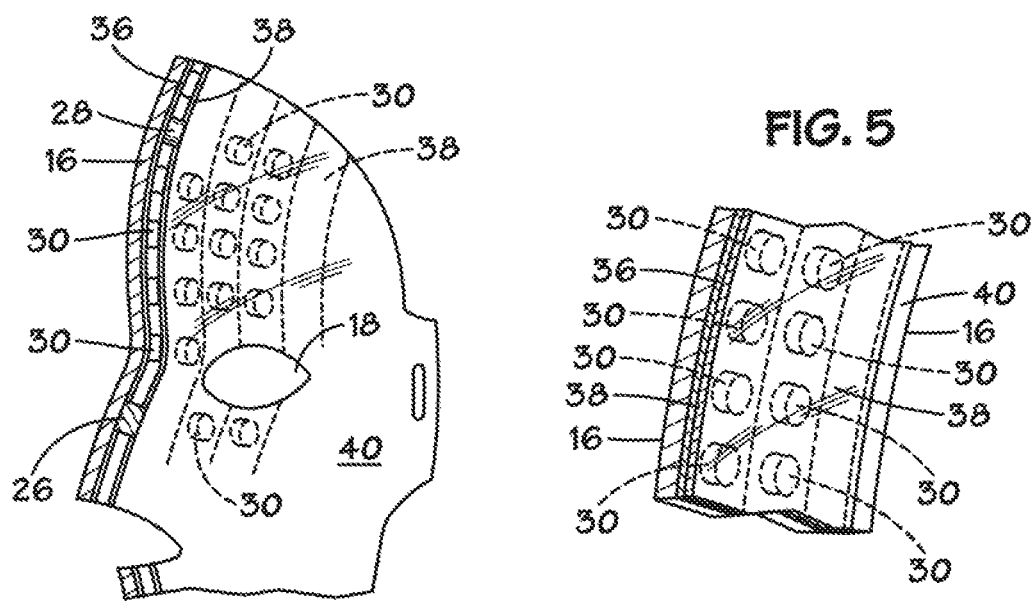
FIG. 5
FIG. 4

PHOTOTHERAPY MASK WITH QUANTUM DOT PHOSPHORS

CROSS-REFERENCE TO RELATED APPLICATIONS

This application claims the benefit of U.S. Provisional Application No. 62/300,484, filed on Feb. 26, 2016, the contents of which is hereby incorporated by reference in its entirety.

STATEMENT REGARDING FEDERALLY SPONSORED RESEARCH OR DEVELOPMENT

Not Applicable

BACKGROUND OF THE INVENTION

1. Field of the Invention

The present invention generally relates to phototherapy devices. More specifically, it relates to phototherapy devices comprising semiconductor nanoparticles ("quantum dots") that adjust the light used to certain wavelength(s).

2. Description of the Related Art including information disclosed under 37 CFR 1.97 and 1.98

The term phototherapy literally means the use of light to treat medical conditions. It is used to treat common skin conditions such as psoriasis, atopic eczema, acne, and the like. Other common names include: light boxes, bright light treatment, ultraviolet light therapy, UV, ultraviolet blood irradiation, colored light therapy, chromatotherapy. Within the scientific and medical communities, phototherapy is also referred to as ultraviolet phototherapy, photopheresis, extracorporeal photochemotherapy, and photodynamic therapy.

Light therapy involves the use of visible light or non-visible ultraviolet light to treat a variety of conditions.

Medical professionals may prescribe the use of light boxes, photopheresis, photodynamic therapy, or UV light therapy. These are typically used to treat conditions for which studies have shown the methods to be safe and effective. For example, the use of light boxes to mimic sunlight is a proven medical treatment for seasonal affective disorder (SAD). Ultraviolet (UV) light therapy is used to treat psoriasis and cutaneous T-cell lymphoma (a type of cancer that first appears on the skin). Photodynamic therapy is helpful in treating certain cancers or precancers of the skin, esophagus, and lungs, and is now being tested against other types of cancer. A special form of UV blood irradiation, called photopheresis or extracorporeal photochemotherapy, also inhibits T-cell lymphoma and may be helpful for other conditions.

Colored light therapy involves the use of colored lights such as blue, red, and violet lights that the practitioner shines directly on the patient. In some cases, the patient purchases the device and uses it at home in this alternative use of light therapy. Sometimes the lights flash in patterns.

One type of light therapy is used in conventional medicine for newborns who have a buildup of a waste product called bilirubin in the blood. The infant's skin is exposed to a special blue light, usually for several days. This helps the bilirubin to break down into a substance that is easier for the baby to excrete.

Light boxes contain lights that simulate the wavelengths of sunlight, and are used in mainstream medicine. Patients getting this kind of treatment sit in front of the light box or special bright lamp for a prescribed amount of time each day. The person may read or do other tasks during the light exposure, but must sit close enough to the light to receive its full effect. The amount of time required will vary according to the person and the strength of light being used. For most people with SAD, light treatment is used early in the morning from thirty minutes to two hours each day. A brighter light may require less time exposure.

In ultraviolet light therapy, the eyes and unaffected skin are protected while the patient is exposed to UV light for a prescribed length of time. This conventional treatment for psoriasis may involve the use of UV light and drugs that make the skin sensitive to UV light. A newer type of UV light source, called narrow-band UV light, is also being used now and may be preferred over broad-band UV light.

Ultraviolet blood irradiation is called photopheresis or extracorporeal photochemotherapy in conventional medicine and is mainly used to inhibit T-cell lymphoma. It may also be helpful for other conditions. During this procedure, blood is removed from the patient and separated into different types of cells. About a pint of blood, mostly white blood cells, is treated with a special drug to make it make it more sensitive to light. It is then treated with UV light, and the blood is infused back into the patient. This procedure is considered a form of immunotherapy and takes from three to five hours.

Photodynamic therapy is used in conventional medicine for certain types of cancer. The patient is given a drug to make cancer cells more sensitive to light. The tumor area is then exposed to laser or another type of light.

Ultraviolet light therapy (phototherapy) is commonly used to treat psoriasis. There is also evidence that UV light therapy inhibits the growth of cutaneous T-cell lymphoma (a type of skin lymphoma). Researchers have found that when used along with other treatment, it has resulted in long-term remission and cure among many patients in the early stage of the disease. In patients who were treated later in the disease, it has prolonged survival. Early studies suggest that certain types of UV light may also be helpful for people with atopic dermatitis (an allergic skin condition) and vitiligo (uneven pigment in the skin).

Ultraviolet blood irradiation treatment is approved by the U.S. Food and Drug Administration (FDA) for treating T-cell lymphoma involving the skin. Photopheresis is sometimes used conventionally when organ transplant rejection or graft-versus-host disease (a complication related to bone marrow or stem cell transplants) does not respond to usual conventional treatments. Some clinical trial results appear promising for the treatment of immune system diseases such as multiple sclerosis, systemic sclerosis, rheumatoid arthritis, lupus, and type 1 diabetes.

Light therapy that involves only visible light (light boxes and colored light therapy) is generally considered safe. Any treatment that exposes the patient to ultraviolet radiation presents some danger, including premature aging of the skin and an increased risk for skin cancer later in life.

People who get long-term UV light treatment for psoriasis or other conditions may have a greater-than-average number of cataracts and skin-related problems, including cancer. They may also be at higher risk of sunburn the day of UV treatment and are advised to avoid natural sunlight.

A flexible organic light emitting diode (FOLED) is a type of organic light-emitting diode (OLED) incorporating a flexible plastic substrate on which the electroluminescent organic semiconductor is deposited. This enables the device to be bent or rolled while still operating. Flexible OLEDs form the basis of one method of fabricating a rollable display.

An OLED emits light due to the electroluminescence of thin films of organic semiconductors approximately 100 nm thick. Regular OLEDs are usually fabricated on a glass substrate, but by replacing glass with a flexible plastic such as polyethylene terephthalate (PET) among others, OLEDs can be made both bendable and lightweight.

Such materials may not be suitable for comparable devices based on inorganic semiconductors due to the need for lattice matching and the high temperature fabrication procedure involved.

In contrast, flexible OLED devices can be fabricated by deposition of the organic layer onto the substrate using a method derived from inkjet printing, allowing the inexpensive and roll-to-roll fabrication of printed electronics.

Flexible OLEDs may be used in the production of rollable displays, electronic paper, or bendable displays which can be integrated into clothing, wallpaper or other curved surfaces. Prototype displays have been exhibited that are capable of being rolled around the width of a pencil.

Current phototherapy masks are limited by:
Available area to populate with LED's
Fixed wavelengths
Varying distance across areas of the face
Distance from user's skin required for even distribution of light and alters light delivery
Variability of peak wavelength
Cost can be prohibitive
Performance trade-off between professional (clinical) and home-use devices

BRIEF SUMMARY OF THE INVENTION

An exemplary phototherapy mask according to the invention comprises a rigid (or semi-rigid) shell contoured to the human face. A flexible array of LEDs is affixed to the inner surface of the mask. A flexible, quantum dot-containing film is situated over the flexible array of LEDs. The quantum dots in the QD-containing film are selected to photo-luminesce at one or more particular wavelengths in response to photoexcitation by the light emitted from the LEDs. The LEDs emit "primary light" and the quantum dots down-convert at least a portion of the primary light to "secondary light." The flexible, quantum dot-containing film may be interchangeable such that the wavelength(s) of the secondary light may be tailored to various phototherapy treatment regimes.

A phototherapy mask according to the present invention provides the following advantages:
Flexible LED array follows contours of mask
Replaceable quantum dot film (tailored to desired spectrum)
Quantum dots used may be free of toxic heavy metals
Different films (containing quantum dots tuned for different wavelengths) for different treatments
Limited distance variation of light source from skin
Portable versions possible (with battery-based power pack)
Clinic-level performance at home-use device prices
Convenience

BRIEF DESCRIPTION OF THE SEVERAL VIEWS OF THE DRAWING(S)

FIG. 3 is a side view, partially in cross section of the mask shown in FIG. 1 being worn by a user.

FIG. 4 is a cross-sectional view of a portion of the mask shown in FIG. 3.

FIG. 5 is a fragmentary, enlarged view of a portion of the inside surface of the mask shown in FIGS. 1-4.

DETAILED DESCRIPTION OF THE INVENTION

Figure 1:
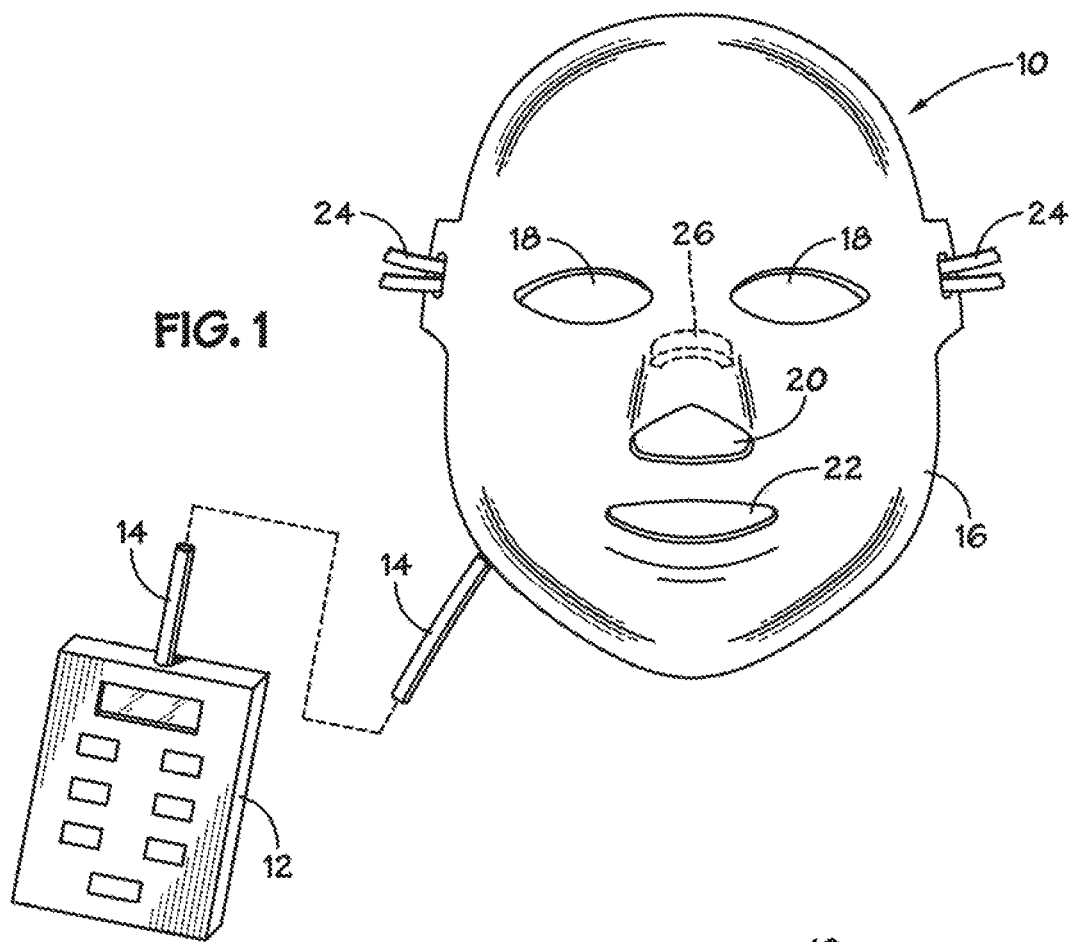
FIG. 1 is a front view of a phototherapy mask and its associated power controller according to an embodiment of the invention.

The invention may best be understood by reference to the drawing figures wherein the following reference numbers are used:
10 mask
12 power controller
14 power cable
16 shell
18 eye openings
20 nose opening
22 mouth opening
24 attachment straps
26 nose bridge
28 standoffs
30 primary light source
32 user's ear
34 user's head
36 primary light source substrate
38 QD-containing film (secondary light source)
40 inner surface of shell In certain embodiments, the invention may comprise a face mask having a primary light source providing light at a first wavelength and a secondary light source that emits light at a second wavelength in response to excitation by light from the primary light source.

The primary light source may be an array of light-emitting diodes (LEDs). The LED array may be a flexible LED array. The flexible LED array may be an OLED array on a flexible substrate.

The first wavelength may be in the blue portion of the electromagnetic spectrum. In other embodiments, the first wavelength may be in the UV portion of the electromagnetic spectrum. In yet other embodiments, the primary light source may comprise a plurality of light-emitting devices that emit at different wavelengths. By way of example only, the primary light source may comprise a first set of LEDs that emit in the ultraviolet region of the spectrum interspersed with a second set of LEDs that emit in the blue portion of the spectrum.

The light reaching the face of a user of the phototherapy mask may be a blend of the primary light and the secondary light.

The secondary light source may comprise fluorescent material. In certain embodiments the fluorescent material may comprise quantum dots. The quantum dots may be CFQD® heavy metal-free quantum dots [Nanoco Technologies Ltd., 46 Grafton St., Manchester M13 9NT, U.K.] Many types of quantum dots will emit light of specific frequencies if electricity or light is applied to them, and these frequencies can be precisely tuned by changing the size, shape and material of the QDs, giving rise to many applications. Thus, the characteristics of the secondary light may be optimized by appropriate selection of the quantum dots in a quantum dot-containing film.

In a face mask according to the invention, the second wavelength may be longer than the first wavelength. In certain embodiments, the secondary light may comprise a plurality of different wavelengths.

The secondary light source may comprise a flexible polymer film that incorporates quantum dots. In certain embodiments, the flexible polymer film comprises barriers to oxygen and water vapor. In certain embodiments the flexible polymer film may comprise quantum dots dispersed in a resin sandwiched between two barrier films such as TBF1004 barrier film available from i-Components Co., Ltd. [701, Family Tower, 958-2, Youngtong-dong, Paldal-gu Soowon-si, Gyeonggi-do, S. Korea] The resin may be a two-phase resin system. Multi-phase and two-phase polymer films containing heavy metal-free semiconductor nanoparticles dispersed in an inner phase which is then dispersed in a suitable gas barrier outer phase have been described previously—see, e.g., U.S. Pub. No. 2015/0047765 "Quantum dot films utilizing multi-phase resin" and U.S. Pub. No. 2015/0275078 "Quantum dot compositions." Highly stable films containing quantum dots may be prepared from resins containing a fast-curing inner phase having a high glass transition temperature ($T_g$) and certain inner phase/outer phase combinations. Such films are disclosed in commonly-owned U.S. patent application Ser. No. 15/429,845 filed on Feb. 10, 2017.

In certain embodiments, the quantum dots in the quantum dot-containing film may be encased in polymer beads.

In a face mask according to the invention, the flexible polymer film may be adjacent the primary light source or spaced apart from the primary light source to allow better dispersion of the light before it enters the flexible polymer film. In certain embodiments, the flexible polymer film may be at a substantially constant distance from the primary light source at all locations on the mask. The face mask may be configured such that the flexible polymer film is at a substantially constant distance from the skin of a user wearing the mask. In certain embodiments, the flexible polymer film may be replaceable.

The flexible polymer film may comprise at least one scattering agent. One example of a suitable scattering agent is barium sulfate.

In certain embodiments, the flexible polymer film comprises quantum dots that fluoresce in the infrared portion of the electromagnetic spectrum.

In one particular embodiment of the invention, the face mask comprises a primary light source providing light at a first wavelength and a third wavelength, said third wavelength being in the infrared portion of the electromagnetic spectrum, and a secondary light source that emits light at a second wavelength in response to excitation by light at the first wavelength from the primary light source.

Certain embodiments of the invention may comprise a flexible LED array such as is available from Design LED Products Ltd. [Alba Innovation Centre, Alba Campus, Livingston EH54 7GA, U.K.].

LED ribbon strips may be used as the primary light source in a phototherapy mask according to the invention. "LED ribbon lights" are substantially flat. The LEDs are mounted directly on the surface of a flexible LED circuit board. In certain embodiments, a cut-to-fit LED array such as DIODE LED® tape LEDs [ELEMENTAL LED, INC. 1195 PARK AVE., SUITE 211 EMERYVILLE CALIF. 94608] may be used.

Certain embodiments of the invention may comprise a portable power supply which may have replaceable batteries or rechargeable batteries.

Yet other embodiments of the invention comprise other form factors or bespoke masks for seasons or with personalisation. Still other embodiments include wearable wound healing equipment and devices targeted specifically for light therapy in hospitals and the home. For example, a flexible LED array combined with a flexible QD-containing film (but without the rigid or semi-rigid shell of a face mask) could be wrapped around a patient's extremity.

EXAMPLE

Figure 2:
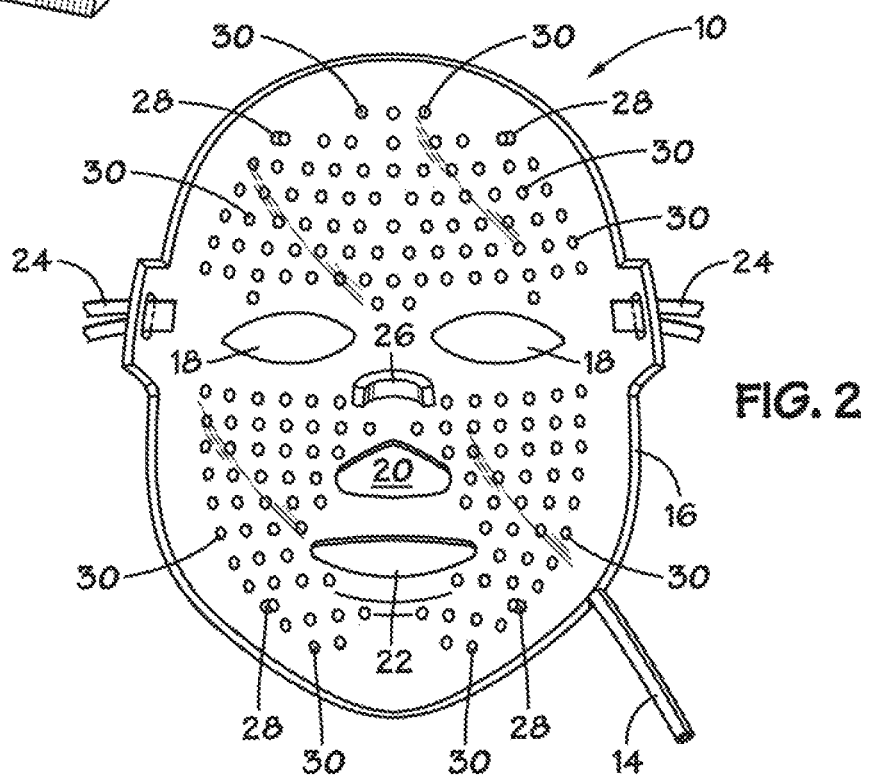
FIG. 2 is a rear view of the mask shown in FIG. 1

An illustrative example of a phototherapy facemask according to an embodiment of the invention is illustrated in FIGS. 1-5.

Facemask 10 comprises a rigid (or semi-rigid) shell 16 contoured to the human face. Shell 16 may be fabricated of any suitable material. In the illustrated embodiment, shell 16 comprises a molded, thermoplastic polymer. Any other suitable material may be use. Optionally, openings 18, 20, and 22 may be provided in shell 16 for the user's eyes, nose and mouth, respectively.

A flexible array of LEDs 30 is affixed to the inner surface 40 of the mask and provided with suitable power connections. LEDs 30 may be surface mounted to substrate 36 which may be a flexible tape.

In the illustrated portable embodiment, power controller 12 is connected to LEDs 30 via power cable 14. Power controller 12 may comprise replaceable batteries or rechargeable batteries. In yet other embodiments, the primary light sources 30 are powered from the mains.

A flexible, quantum dot-containing film 38 is situated over the flexible array of LEDs 30. The quantum dots in the QD-containing film are selected to photo-luminesce at one or more particular wavelengths in response to photoexcitation by the light emitted from the LEDs. The LEDs emit "primary light" and the quantum dots down-convert at least a portion of the primary light to "secondary light." The flexible, quantum dot-containing film 38 may be interchangeable such that the wavelength(s) of the secondary light may be tailored to various phototherapy treatment regimes. Releasable fasteners (not shown) may secure quantum dot-containing film 38 in place.

Mask 10 may be equipped with attachment straps 24 to secure the mask over the user's face. In the illustrated embodiment, attachment straps 24 are configured to loop over a user's ear 32. Other means of securing mask 10 to a user's head 34 may be used and will be readily apparent to those skilled in the art. Mask 10 may be equipped with standoffs 28 and/or nose bridge 26 to position the mask at a selected distance from the user's face. In one particular, preferred embodiment, the contours of the mask acting in concert with standoffs 28 result in the quantum dot-containing film 38 being positioned at a substantially uniform distance from the user's face. In certain embodiments, mask 10 is provided in a range of sizes and/or shapes to more nearly match the size and shape of a certain user's face.

In certain embodiments (not shown) an inner shell may be provided having corresponding openings 18, 20 and 22 for the user's eyes, nose and mouth, respectively. The inner shell may be transparent or translucent. Standoffs 28 and nose bridge 26 may be mounted to the inner surface of the inner shell. The inner shell may protect QD-containing film 38 from perspiration, skin oils, and physical damage.

The foregoing presents particular embodiments of a system embodying the principles of the invention. Although these embodiments of the invention have been shown and described, they are not intended to limit what this patent covers. Those skilled in the art will understand that various changes and modifications may be made without departing from the scope of the present invention as literally and equivalently covered by the following claims.

What is claimed is:

1. A phototherapy method comprising:
providing a shell having eye openings and an inner surface contoured to a user's face;
providing a flexible array of light-emitting diodes affixed to the inner surface of the shell;
providing a first, interchangeable, flexible quantum dot-containing film substantially covering the array of light-emitting diodes, said first, flexible quantum dot-containing film emitting light at a first wavelength in response to photo-excitation by light from the array of light-emitting diodes;
exposing the face of a patient wearing the shell provided with the flexible array of light-emitting diodes affixed to the inner surface of the shell and the first, replaceable, flexible, quantum dot-containing film substantially covering the array of light-emitting diodes to light of the first wavelength by activating the light-emitting diodes for a first period of time;
replacing the first, interchangeable, flexible, quantum dot-containing film with a second, flexible, quantum dot-containing film said second, flexible, quantum dot-containing film emitting light at a second wavelength in response to photo-excitation by light from the array of light-emitting diodes; and
exposing the face of a patient wearing the shell provided with the flexible array of light-emitting diodes affixed to the inner surface of the shell and the second, flexible, quantum dot-containing film substantially covering the array of light-emitting diodes to light of the second wavelength by activating the light-emitting diodes for a second period of time.

2. A phototherapy system, the system comprising:
a face mask configured to emit electromagnetic radiation over at least a portion of the face of a user wearing the mask, the face mask comprising:
a shell contoured to fit over at least a portion of a user's face and having eye openings;
a primary light source having a first surface and a second surface opposite the first surface, the first surface affixed to an inner surface of the shell, the primary light source configured to emit light at a first wavelength directed toward a portion of the user's face; and
a plurality of flexible polymer films, each flexible polymer film comprising quantum dots configured to emit light in response to excitation by light from the primary light source,
wherein each flexible polymer film is configured to be interchangeably placed on the second surface of the primary light source to substantially cover the primary light source, and
wherein each of the plurality of flexible polymer films comprise a different type of quantum dots, each different type of quantum dots configured to emit light at a different wavelength.

3. The phototherapy system of claim 2 wherein the first wavelength is in the blue portion or the UV portion of the electromagnetic spectrum.

4. The phototherapy system of claim 2, wherein the primary light source is coupled with an external power controller by a power cable.

5. The phototherapy system of claim 2 wherein each of the plurality of flexible polymer films comprise the quantum dots dispersed in a two-phase resin system between two sheets of a transparent or translucent barrier film.

6. The phototherapy system of claim 2 wherein each of the plurality of flexible polymer films has a particular use in a particular treatment.

7. The phototherapy system of claim 2, wherein the primary light source is an array of light-emitting diodes (LEDs).

8. The phototherapy system of claim 7, wherein the LED array is a flexible LED array.

9. The phototherapy system of claim 2, wherein the quantum dots are heavy metal-free quantum dots.

10. The phototherapy system of claim 2, wherein the flexible polymer films comprise barriers to oxygen and water vapor.

11. The phototherapy system of claim 2, wherein the face mask further comprises at least one of a plurality of standoffs or a nose bridge, the plurality of standoffs and the nose bridge configured such that each flexible polymer film, when interchangeably placed on the surface of the primary light source opposite the inner surface of the shell, is at a substantially constant distance from the skin of the user when the user is wearing the mask.

12. The phototherapy system of claim 2, wherein the flexible polymer films comprise at least one scattering agent.

13. The phototherapy system of claim 2, wherein at least one of the plurality of flexible polymer films comprises quantum dots that fluoresce in the infrared portion of the electromagnetic spectrum.

14. The phototherapy system of claim 2, wherein the primary light source is further configured to provide electromagnetic radiation in the form of light at a third wavelength directed toward the skin of the user, said third wavelength being in the infrared portion of the electromagnetic spectrum.

* * * * *